United States Patent [19]
Ester

[11] 3,989,762
[45] Nov. 2, 1976

[54] PROCESS FOR THE MANUFACTURE OF ALCOHOLS BY THE HYDRATION OF OLEFINS

[75] Inventor: Wilhelm Ester, Herne, Germany

[73] Assignee: Veba-Chemie AG, Gelsenkirchen-Buer, Germany

[22] Filed: Nov. 25, 1970

[21] Appl. No.: 92,821

Related U.S. Application Data

[63] Continuation-in-part of Ser. No. 813,311, April 3, 1969, abandoned.

[30] Foreign Application Priority Data
Dec. 1, 1969  Germany.............................. 1960139

[52] U.S. Cl................................ 260/641; 203/99; 260/677 A
[51] Int. Cl.²......................................... C07C 29/04
[58] Field of Search..................................... 260/641

[56] References Cited
UNITED STATES PATENTS

| | | |
|---|---|---|
| 1,951,740 | 3/1934 | Shiffler et al. ...................... 260/641 |
| 2,050,442 | 8/1936 | Metzger.............................. 260/641 |
| 2,050,444 | 8/1936 | Metzger.............................. 260/641 |
| 2,052,806 | 9/1936 | Shiffler et al. ...................... 260/641 |
| 2,107,065 | 2/1938 | Peski................................... 260/641 |
| 2,617,834 | 11/1952 | Woodbridge ....................... 260/641 |
| 2,663,744 | 12/1953 | Lukasiewicz et al. .............. 260/641 |
| 3,311,568 | 3/1967 | Klimenko............................ 260/641 |
| 3,459,678 | 8/1969 | Hagemeyer et al................. 260/641 |

FOREIGN PATENTS OR APPLICATIONS

| | | |
|---|---|---|
| 1,018,201 | 10/1952 | France............................... 260/641 |
| 1,193,929 | 6/1965 | Germany ........................... 260/641 |

*Primary Examiner*—Joseph E. Evans
*Attorney, Agent, or Firm*—Burgess, Dinklage & Sprung

[57] ABSTRACT

In the process of production of alcohol by hydration of olefin by reacting water and olefin in a reaction zone, for conversion of the olefin to the alcohol, wherein following the hydration unreacted olefin is separated from the effluent from the reaction zone and recycled to the reaction zone, the improvement which comprises maintaining the concentration of olefin at more than 90 vol.% based on the combined composition of the recycle stream and make-up olefin introduced into the process, as gas. The effluent of the hydration reaction can be separated into an alcohol fraction and a gaseous residue fraction; the residue fraction can be distilled into an overhead fraction and a sump fraction, and the overhead fraction can be employed as the recycle stream. Impurities in the system even though lower boiling than the olefin can be removed in the sump product of the distillation to control the concentration of such impurities in the recycle stream.

8 Claims, 1 Drawing Figure

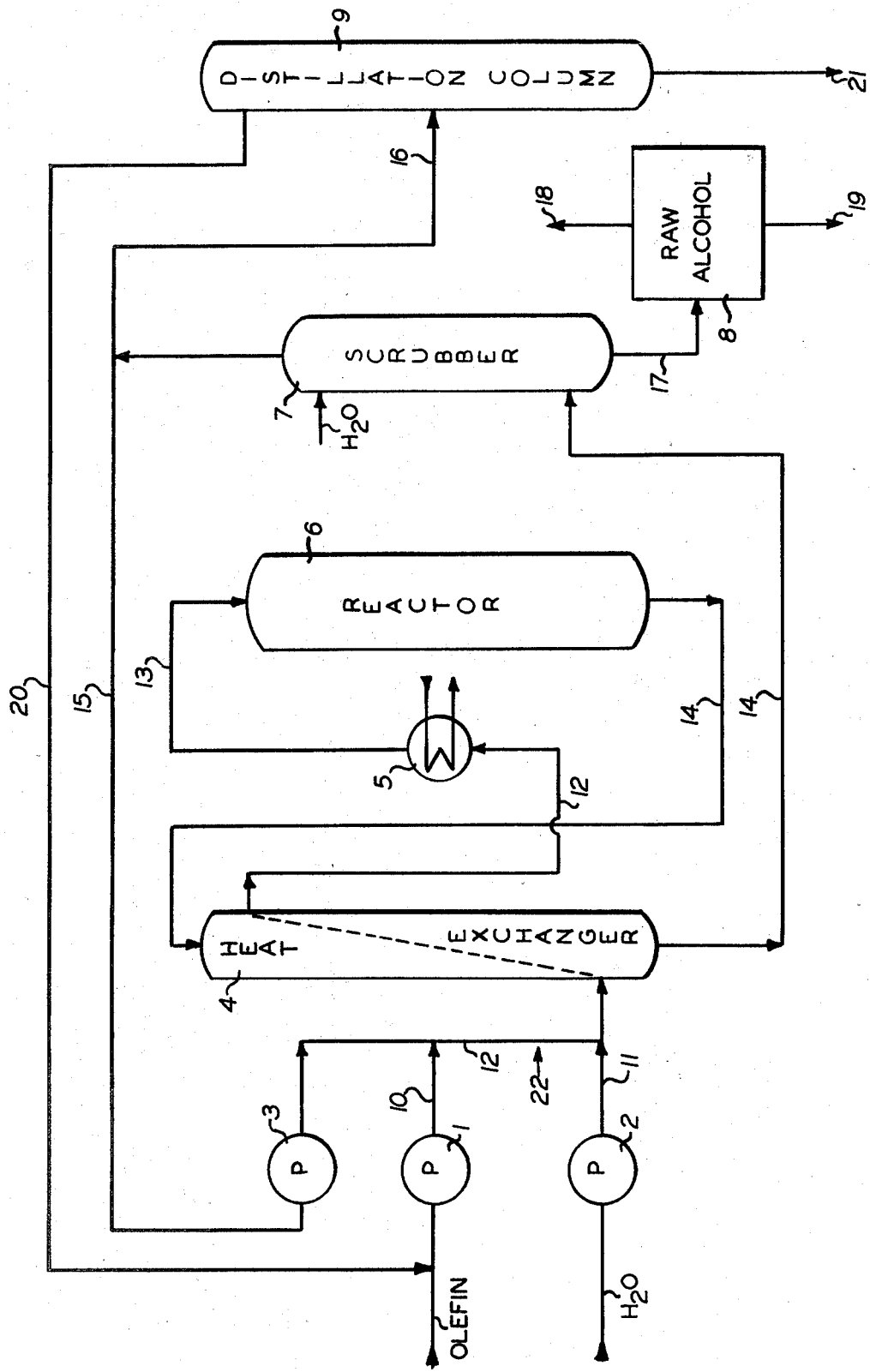

3,989,762

PROCESS FOR THE MANUFACTURE OF ALCOHOLS BY THE HYDRATION OF OLEFINS

This application is a continuation-in-part of application Ser. No. 813,311, filed Apr. 3, 1969, now abandoned.

BACKGROUND

The invention concerns a process for the catalytic hydration of lower olefins, e.g. especially ethylene or propylene, and also butenes, on a solid bed catalyst to form the corresponding alcohols in the gas phase or gas-liquid phase.

It is in the prior art to make alcohols by the direct gas-phase hydration of olefins. The customary technique consists in operating not only at elevated pressure but also with very great amounts of circulating gas owing to the unfavorable equilibrium situation at the reaction temperature that are applied.

In the prior art process it is common practice to keep the concentration of the circulating gas at approximately 85% by volume. This is based on the consideration that, with a higher circulating gas concentration, the transformation at the catalyst increases while the energy cost and invested costs are lower, but at the same time the amount of gas that has to be purged increases considerably because the impurities can accumulate in the circulating gas to only a slight degree. If, however, a lower concentration of olefin in the circulating gas is used, i.e., a substantially higher concentration of impurities in the circulating gas, the amount of gas that has to be purged decreases considerably. The use of circulating gas concentrations substantially below 85% by volume is not considered, however, because in that case the olefin transformation per passage, under otherwise constant conditions, diminishes virtually in proportion to the reduction of the olefin concentration in the circulating gas.

The impurities that have to be purged from the circulating gas are, on the one hand, substances which are brought in with the olefin input, and, on the other hand, by-products which form during the hydrations of olefins. The impurities brought in with the olefin input are substances of which some boil lower than the olefin—methane and nitrogen in the case of ethylene (ethanol production)—and some boil higher, such as ethane and $C_3$ hydrocarbons; in the case of propylene (isopropanol production) the impurities include ethylene in addition to methane and nitrogen as the substances which boil lower than propylene, and the higher boiling impurities are propane and $C_4$ hydrocarbons. The by-products that form during the hydration are particularly olefin polymers of low molecular weight, such as dimers, trimers and tetramers, which can form the corresponding alcohols during the reaction at the catalyst, and the corresponding saturated hydrocarbons.

Separation of these alcohols from the principal alcohol product is not easy. The olefin polymers of low molecular weight, however, can also be further polymerized to higher hydrocarbons which are entrained in the form of fine mists with the circulation gas and are extremely difficult to separate. By coating the catalyst, they reduce its activity and shorten its life.

The gas that is purged has hitherto been burned off, or it has been used in a system permitting the utilization of olefins of low concentration (e.g., alkylation of benzene), or it has been fed back into the olefin producing system, or it has been put through a distillation process at the plant.

The distillation process, according to the state of the art, is performed at low to medium pressures and correspondingly low temperatures, i.e., under conditions that are far below the critical characteristics of the olefins. The disadvantage of this procedure is to be seen in the fact, among others, that multi-stage refrigeration units have to be used for the condensation, along with columns of relatively large radius; also, on account of the higher heat of evaporation of the olefins, a high expenditure of energy is required at low temperatures for the evaporation and condensation. In the distillative separating process that has hitherto been customary in the art (Ullmann, "Enzyklopädieder technischem Chemie," 3rd Edition, Vol. 10, pp. 150–161) for low-boiling olefins, two columns are necessary for the separation of low boiling and high boiling impurities, the low boiling impurities being separated in the first column, while in the second column the higher boiling impurities are drawn off from the sump of the column and the concentrated olefin is drawn off at the head of the column.

THE INVENTION

It has now been found that, contrary to the general rules of kinetics, according to which reaction of the reactants would increase at higher concentrations thereof, and thus in the present case an increase in formation of polymers would occur, the formation of the low polymers diminishes as the olefin concentration in the circulating gas increases.

The greatly diminished formation of low polymers is also accompanied by a reduction in the formation of the more highly polymerized products, which otherwise are undesirably entrained in the circulation in the form of mists which in part are deposited on the catalysts, e.g. the solid bed catalysts; thus resulting in a loss of activity.

The subject of the invention, therefore, is a process for the catalystic hydration of olefin, with 2–4 carbon atoms to the corresponding alcohol in the gas phase, the concentration in volume percent of the olefinic gas in circulation (measured after addition of the olefin feed and before addition of the water feed) amounting to more than 90% of said circulating stream, e.g. 90–98%, and preferably being between 95% and 97%. The invention particularly contemplates the hydration of ethylenically unsaturated olefins such as ethylene, propene, and the butylenes (all of the butylenes). The reaction can be carried out at elevated temperature and pressure known for the hydration, for example at a temperature of about 140°–320° C, and at a pressure of about 10–100 atm. gauge. As mentioned, catalysts known for the reaction can be used.

So, at circulating gas concentrations in excess of 90%, the formation of low olefinic polymers is to a great extent suppressed, and with it the formation of higher alcohols or their further polymerization to higher hydrocarbon oils. Moreover, this reduction of polymerization does not take place in a proportional relationship to a step-by-step increase in the circulating gas concentration. The reduction of the formation of butene, for example, is especially great in the concentration range of about 90% to 92% in the case of ethylene, whereas, above a concentration of about 97%, practically no further diminution in the formation of low polymers is brought about.

The amount of olefin in the circulating stream is fixed by purging recycle gas and by introducing fresh olefin to obtain the desired olefin concentration.

Thus, the invention is concerned with a process for production of an alcohol by hydration of olefin by reacting water and olefin, containing impurities, in a reaction zone for conversion of the olefin to alcohol, and the production of by-products of the reaction. Following the hydration reaction, unreacted olefin, by-products of the reaction, and impurities are separated from alcohol produced in the reaction and recycled to the reaction zone. Make-up olefin and water are added to the recycle stream. According to the invention, the concentration of the olefin is maintained at more than 90 vol.%, based on the combined composition of the recycled stream and the make-up olefin, as gas.

In the process, following the hydration reaction, the effluent thereof can be separated into an alcohol fraction and a residue fraction, e.g. a gaseous residue fraction, and the said residue fraction can be distilled into an overhead fraction and a sump fraction and said overhead fraction can be employed as the recycle stream. Impurities including compounds lower boiling than the olefin are present in the recycle stream and in the said sump fraction, and the concentration of the lower boiling impurities in the recycle stream can be controlled by removal from the process of lower boiling impurities contained in the sump fraction.

POLYMER FORMATION AND CATALYST ACTIVITY

Tables 1, 3 and 5 set forth a comparison of circulating gas concentration and the formation of low polymers, and Tables 2 and 4 reflect the lows of catalyst activity in relation to the circulating gas concentration.

Operating conditions for the processes of Tables 1 and 2: The hydration catalyst was prepared according to W. German Pat. No. 1,156,772, the temperature upon entering the catalyst furnace was 250° C, the molar ratio of ethylene to water was 1 : 0.85, and the working pressure was 70 atmospheres gauge.

Operating conditions for the processes of Tables 3 and 4: The hydration catalyst was prepared according to W. German Pat. No. 1,156,772, except that it was impregnated with 35% phosphoric acid. The temperature upon entering the catalyst furnace was 215° C, the molar ratio of propylene to water was 1 : 0.98, and the working pressure was 40 atmospheres gauge.

The catalyst used for the tests was mineral aluminum silicate in the form of pellets with 5 mm diameter (mfr.: Südchemie, trademark name K 306) and was pretreated according to the Western German Pat. No. 1,156,772 in the following manner:

750 kg of K 306 pellets are refluxed at 100°–110° C with 1375 kg of 11% hydrochloric acid for 10 hours. Then 400 liters of hydrochloric acid are drained out and replace with 400 liters of 30% hydrochloric acid, so that the total acid concentration amounts to about 17%. After an additional boiling time of 14 hours, all of the acid is drained out and the catalyst is boiled for one hour with enough desalted water to fully cover it. Then the wash water is drained off and again replaced by the same amount of fully desalted water, which is also drained off after one hour of boiling time. This procedure is repeated 16 times. The final wash water that drains out is then free of chloride and aluminum ions. The catalyst is dried by the injection of dry air at 120° C. The catalyst at this point still contains 3.7% $Al_2O_3$. The catalyst is then impregnated with 74% $H_3PO_4$. The excess phosphoric acid is drained away, and the catalyst is dried with hot air at about 100° C.

Operating conditions for the process of Table 5: The hydration catalyst was prepared as in the process of Tables 3 and 4, the temperature upon entering the catalyst furnace was 195° C, the molar ratio of butene-1 to water was 1 : 1.05, and the working pressure was 25 atmospheres gauge.

Table 1

Formation of butenes in relation to the ethylene concentration in the circulating gas.

| Volume-% of ethylene in circulating gas | Butenes formed as weight percentage of the ethanol formed |
|---|---|
| 85 | 0.35 |
| 90 | 0.21 |
| 92 | 0.09 |
| 94 | 0.06 |
| 96 | 0.04 |
| 98 | 0.03 |

Table 2

Loss of catalyst activity

| Volume-% of ethylene in circulating gas | % of activity loss after | | | |
|---|---|---|---|---|
| | 1000 h | 2000 h | 4000 h | 8000 h |
| 85% | 1.5 | 3.2 | 5.9 | 15.7 |
| 90% | 0.3 | 0.5 | 1.1 | 3.9 |
| 95% | 0.2 | 0.4 | 0.6 | 2.0 |

Table 3

Formation of hexenes in relation to the concentration of propylene in the circulating gas

| Volume-% of propylene in the circulating gas | Hexenes formed, as weight percentage of the 150 isopropanol formed |
|---|---|
| 85 | 0.21 |
| 90 | 0.16 |
| 93 | 0.07 |
| 96 | 0.03 |
| 99 | 0.03 |

Table 4

Loss of catalyst activity

| Volume-% of propylene in the circulating gas | Activity loss in % after | | | |
|---|---|---|---|---|
| | 1000 h | 2000 h | 4000 h | 8000 h |
| 85 | 1.1 | 2.4 | 5.1 | 11.6 |
| 90% | 0.2 | 0.4 | 0.8 | 2.1 |
| 96% | 0.1 | 0.3 | 0.5 | 1.3 |

Table 5

Formation of octenes in relation to the concentration of butene-(1) in the circulating gas

| Volume-% of butylene in the circulating gas | Octenes formed, as weight percentage of the secondary butanol formed |
|---|---|
| 85 | 0.20 |
| 90 | 0.15 |
| 93 | 0.05 |
| 96 | 0.02 |
| 99 | 0.02 |

DISTILLATION

In a preferred embodiment, the invention involves concentrating by distillation the olefin containing gas stream which is obtained by condensation and washing of the mixture leaving the reaction chamber to recover the alcohol, this being done in such a manner that, after the feed back of the gas, olefin concentration of more than 90% by volume, preferably 95 to 97% by volume, establishes itself.

It has furthermore surprisingly been found that, contrary to the prejudice existing in the art, the olefins of low molecular weight, such as the $C_2$–$C_4$ olefins, especially ethylene and propylene, can be purified and concentrated, in the mentioned distillation, to advantage under working conditions close to the critical characteristics of these olefins. In this manner it is possible to purify the gas obtained from the hydration of olefins at higher pressures and temperatures than customary hitherto. In this procedure it has surprisingly been found that a portion of the impurities which boil at lower temperatures than the olefin being purified are in the sump of the column and thus can be separated right at this point.

In the procedure of the invention the column for the separation of these lower-boiling impurities is eliminated. An additional surprising advantage of the procedure in the case of distillation conditions close to the critical point of the olefin is to be seen in the fact that the column throughput can be increased to a multiple of the design load without the need of increased power consumption. In spite of the reduction of the reflux in this manner, the separating action of the column continues to be very good. The products which hitherto were unable to be separated or could be separated incompletely at the very best by means of the separating devices commonly used in the art for oil mist can in this manner be separated from the circulating gas easily and completely. In this manner these oil mists are now present in lesser quantity in the olefin that is fed back into the hydration, depending on the input to the concentrating process; the activity and life of the hydration catalyst is extended accordingly. The distillative concentration according to the invention, under conditions close to the critical point of the olefins thus takes place in the presence of oils that form in the hydration, or of washing substances that are foreign to the process. The oils that form in the hydration are mainly hydrocarbons with a boiling range up to 350° C, plus ethers and small amounts of higher alcohols. Washing substances foreign to the process are, for example, paraffin oils of similar boiling range e.g., up to 350° C.

WASHING EXTRACTION

It is assumed that in the process of the invention for the purification of olefins the distillation is accompanied by a washing extraction of the oil mists that are in the circulating gas and which consist mainly of hydrocarbons of high molecular weight, the excellent separating effects being achieved in this manner. The desirability of this practice is borne out by experiments in which a synthetic mixture of pure gases corresponding to the composition of the circulating gas is subjected to the distillation with and without the spray-injection of oil. It was found that the amount of impurities drawn off from the sump of the column when oil injection is used is greater by a factor of 8 than in the case of distillation without the addition of oil.

BY-PRODUCTS AND IMPURITIES

The advantages of the measures taken according to the invention are considerable. The low-boiling impurities always found in the input olefin do not accumulate in the circulating gas. In a simple manner they are removed through the sump of the distillation column together with the higher boiling impurities and the hydrocarbon oils, thereby eliminating the use of special column for the separation of the low-boiling components. Furthermore, ethers and other alcohols can be won from the mixture produced in the sump of the column. Furthermore, it is possible to make the concentration columns considerably smaller in size, the energy consumption is significantly lower on account of the lower heat of evaporation in the vicinity of the critical point, and the liquefaction can be performed relatively easily by a slight removal of heat at a relatively high temperature, so that cheaper coolants can be used. For the restoration of any purified olefin that is drawn off in gaseous form at the head of the column to the working pressure of the hydration system, a correspondingly low amount of power is required, again because of the higher working pressure. Furthermore, the moisture content of the olefin being distilled does not have to comply with very strict requirements, since at elevated temperature there is less danger of the formation of solid hydrates that lead to clogging.

When the procedure of the invention is used, the hydration process takes place more advantageously also, because for an equal olefin content in the circulating gas there is a substantially lower content of oil mists when the measures of the invention are applied. Since some of these oil mists precipitate on the catalyst and thus block its active centers, the loss of catalyst activity is largely prevented in this manner. The improved separation of oil mists from the circulating gas diminishes the density of the latter. From this the hydration process gains the advantage that the energy requirements both of the circulation compressor and of the superheater are reduced.

EXAMPLE 1

Hydration of Ethylene

In a hydration plant depicted in the accompanying flow sheet, the circulation compressor 3 pumps through line 12 into the heat exchanger 4 a quantity of 45,000 Nm³ of ethylene (85% pure); 2100 Nm³/h of fresh ethylene (99.9%) pure is delivered through line 10 from the fresh ethylene compressor 1; and 16 m³/h of deaerated, de-ionized water is fed by the process water pump 2 through line 11. The reactants are heated and evaporated at first in heat exchangers 4 by a countercurrent of the products leaving the reactor 6 and then in the superheater 5 up to the reaction temperature of 265° C. The reactants are feed to the reactor 6 via line 13. The pressure at the inlet to the reactor is 70 atmospheres gauge; the temperature is 265° C. The reactor is filled with 38 m³ of catalyst which has been prepared by leaching a cracking catalyst in the form of balls of about 5 mm diameter made on a basis of bentonite (mfr. Südchemie, trademark name K 306) with hydrochloric acid, followed by soaking with phosphoric acid, in such a manner, that the $Al_2O_3$ content is 3.7%, the pore colume is 0.85 ml per gram of catalyst, the surface area is 185 m²/g catalyst, and the $H_3PO_4$ content after soaking and drying amounts to 41.5% of the total weight. The reaction products are delivered through line 14 to the heat exchanger 4 where they heat the reactants, thereby undergoing cooling and partial condensation. The mixture of gas and liquid is separated in the sump of the scrubber 7, the rising gas is washed free of the alcohol by a countercurrent of 4.5 m³/h of water, at a temperature of 60° C, and is then fed through line 15 to the circulation compressor 3. The liquid that gathers in the sump of the scrubber 7 is flashed in line 17 and stored in the raw alcohol storage tank 8. From here it is fed through line 19 to a distillation column (not shown). The gas 18 that is liberated when the liquid is relieved of pressure (about 75 Nm³/h) is delivered to combustion.

23.0 metric tons of raw alcohol is produced per hour in tank 8, and it has the following composition:
17.4% ethanol
0.32% diethyl ether
0.03% acetaldehyde
0.05% butanols
0.09% hydrocarbons
Remainder: water.

The raw alcohol contains the equivalent of 195 ppm phosphoric acid, the phosphoric acid having been neutralized by the addition of caustic prior to entry via line 14 into the scrubber 7. 4.5 kg of phosphoric acid (reckoned as 100% acid) is sprayed per hour as make-up acid into the free space above the catalyst in the reactor.

From the raw alcohol in line 19, 4.0 metric tons per hour of ethanol are obtained by distillation, corresponding to a yield of 95.0%.

The density of the circulating gas on the discharge side of the circulation compressor 3 amounts to 168 grams per liter (75 atm. gauge and 76° C). For each ton of alcohol produced (reckoned as 100% alcohol), the energy required at the superheater 5 amounts to about $1.725 \times 10^6$ kcal, and the energy required to drive the circulation compressor is about $0.11 \times 10^6$ kcal.

EXAMPLE 2

Hydration of Propylene

In the plant described in Example 1, the following quantities are passed per hour through the catalyst in the reactor:

37,000 Nm³ propylene (85% pure) in the circulation (line 15)

2,000 Nm³ fresh propylene (99.6%) (line 10)

8.5 m³ deaerated, de-ionized process water (line 11)

36 atm gauge pressure at reactor inlet 13

178° C temperature at reactor inlet 13

38 m³ of catalyst containing 26.3% by weight of phosphoric acid.

The circulating gas, from which isopropanol is partially condensed by the cooling in exchanger, is washed at a temperature of 95° C in the scrubber 7 by a countercurrent of 24.5 m³ of water of a temperature of 98° C. A portion of the water produced in the sump of the rectifying column in the distillation of the raw isopropyl alcohol is used as wash water.

The gas 18 that is liberated by the relief of pressure of the alcohol at 8 is partially returned to the process; 120 Nm³ thereof is purged per hour and delivered to combustion, the balance being returned.

4.9 metric tons of isopropyl alcohol are obtained by distillation from the raw isopropyl alcohol in line 19, which corresponds to a yield of 95.8%.

Approximately 36.6 metric tons of raw isopropyl alcohol of the following composition accumulates per hour at 8:
13.45% isopropyl alcohol
0.15% diisopropyl ether
0.005% acetone
0.08% n-propanol
0.04% hexanols
0.03% hydrocarbons
Balance: water The energy comsumption for driving the circulating compressor 3 amounts to $0.09 \times 10^6$ kcal, plus $0.86 \times 10^6$ kcal at the superheater 5 per metric ton of isopropanol produced (reckoned as 100% pure). The density of the circulating gas at the discharge side of the circulation compressor 3 is 128 grams per liter (45.6 atm. gauge and 106° C)

EXAMPLE 3 a. Hydration of Ethylene With Purified Circulating Gas

Instead of purging the 75 Nm³/h of circulating gas out of the system through line 18 as described in Example 1, this amount of gas is compressed with the fresh ethylene compressor 1 and is thus delivered back into the system through line 10. For purging 400 Nm³/h is taken from the circulating gas at the outlet of the scrubber 7 and delivered through line 16 to the distillation column 9. The concentrated head product is carried back through line 20 and mixed into the fresh ethylene while 10 Nm³/h of a gas of the following composition is contained in the sump product and is relieved and burned:

| | |
|---|---|
| Nitrogen | 0.2 Vol.% |
| Methane | 0.4 vol.% |
| Ethane | 19.5 vol.% |
| Ethylene | 47.1 vol.% |
| Isobutane / n-Butane | 15.6 vol.% |
| Butenes | 12.1 vol.% |
| Butadienes | 0.2 vol.% |
| Unknown | 5.0 vol.% |

(For further details, see Example 3b).

Through this procedure, a circulating gas concentration of 95.1 vol.% ethylene is established. Said concentration is in line 12 at the location indicated by 22. The ethylene transformation on the catalyst rises to 2,400 Nm³/h and the ethylene yield increases to 97.4% of the reacted ethylene. The density of the circulating gas at the discharge side of the circulation compressor 3 now amounts to 106 grams per liter (75 atm. gauge and 76° C). The energy consumption for the circulation compressor 3 has dropped to $0.06 \times 10^6$ kcal, and for the superheater 5 it has dropped to $0.56 \times 10^6$ kcal per ton of ethanol produced (reckoned as 100% pure).

Under the conditions of Example 3, the catalyst loses only 12.7% of the activity which it lost under the conditions of Example 1, in a period of 5 months.

b. Separating of the Impurities From the Circulating Gas in the Catalytic Hydration of Ethylene In a sieve tray column 9, 380 mm inside diameter, 78 trays, tray spacing 160 mm, with a circulating evaporator and a reflux condenser flange-mounted on the column, 400 Nm³ of circulating gas, from the scrubber 7, with an ethylene content of 95.1% by volume, together with 0.5 liter of ethylene glycol added to the column feed to prevent hydrate formation, was passed through line 16 and delivered at the 44th tray from the base. The operating pressure at the head of the column amounts to 42 atmospheres gauge, the head temperature 2° C, and the sump temperature 116° C. The steam consumption amounts to $0.048 \times 10^6$ kcal/h.

From the condenser, via line 20, 390 Nm³ is drawn off per hour in gaseous form and fed through the fresh ethylene compressor 1 to the circulating gas. The ethylene concentration at the head amounts to 96.3%. The liquid drawn off from the sump of the column 9 through line 21 is relieved of pressure to separate it into gas and liquid. The gas thus yielded—10 Nm³/h, see Example 3 for composition—is burned. The liquid is separated into two layers in the decanter. The water is separated from the bottom layer by distillation; the ethylene glycol is returned into the column 9. The upper layer—about 40 l/h, can be refined by distillation to diethyl ether. The upper layer contains about 38% diethyl ether, 5.5% $C_2-C_4$ hydrocarbons, 0.3% ethanol and 2.7% butanols. The rest is higher alcohols and hydrocarbons with a boiling range up to 315° C. By elementary analysis, the molecular formula for the mixture boiling above 115° C was determined to be $C_{13}H_{26}O$.

EXAMPLE 4

Hydration of Propylene With Purified Circulating Gas

The plant is operated as in Example 2. By withdrawing 400 Nm³ of circulating gas from the discharge side of the circulating compressor 3, before process water 11 and fresh propylene 10 are fed in, and delivering it to a sieve tray column of 100 trays which is operated at a pressure of 22 atmospheres gauge, a level of 96.2% is established in the circulating gas (at location 22 in line 12). The gas liberated by the expansion of the raw isopropanol at 8, however, is entirely returned through the compressor 1 to the circulating gas. The propylene transformation increases to 2,250 Nm³/h and the yield of isopropanol is 97.6% of the reacted propylene. The density of the circulating gas at the discharge side of the circulating compressor 3, at 45.6 atmospheres gauge and 106° C, amounts to 120.5 grams per liter. The energy consumption for the compressor 3 is measured as $0.05 \times 10^6$ kcal; for the superheater 5 it is $0.48 \times 10^6$ kcal, per ton of alcohol produced (reckoned as 100% pure). The activity loss of the catalyst in the seven-month period amounted to only 27.3% of the loss of activity of the catalyst in Example 2.

What is claimed is:

1. Process for producing alcohols from olefins with olefin recycle which comprises:
    a. hydrating a $C_{2-4}$ olefin containing gas stream wherein the olefin concentration is maintained at more than 90 vol. %, with water in the presence of a hydration catalyst in a hydration zone, said gas stream containing recycled olefin and make-up olefin containing lower and higher boiling impurities;
    b. separating the effluent from the hydration zone into a recycle olefin containing gas stream and an alcohol fraction;
    c. purifying and concentrating the recycle olefin containing gas stream by distillation under temperature and pressure conditions close to the critical point of said olefin, removing
        i. gaseous purified recycle olefin as the head product; and
        ii. the lower and higher boiling impurities present in the make-up olefin and hydrocarbon oils formed during the hydration step as the sump product; and
    d. recycling said purified olefin head product to hydration step (a).

2. Process of claim 1 wherein distillation step (c) is accompanied by a washing extraction of hydrocarbon oil mists formed during the hydration step and present in the olefin containing gas stream.

3. Process of claim 2 wherein paraffin oils having a boiling range up to 350° C are spray injected into the distillation zone as the washing substance.

4. Process of claim 1 wherein the olefin is selected from the group of ethylene, propylene and butylenes.

5. Process of claim 1 wherein the hydration catalyst is a mineral aluminum silicate pretreated with mineral acid to reduce the alumina content thereof to below 10 percent and impregnated with phosphoric acid.

6. Process for claim 1 wherein said olefin is ethylene and alcohol produced is ethanol.

7. Process of claim 1 wherein said olefin is propylene and the alcohol produced is isopropanol.

8. Process of claim 1 wherein ethylene glycol is added to distillation step (c) to prevent hydrate formation.

* * * * *